(12) United States Patent
Marino

(10) Patent No.: US 6,702,113 B2
(45) Date of Patent: Mar. 9, 2004

(54) TOOTHBRUSH SANITIZING ASSEMBLY

(76) Inventor: Anthony J. Marino, 111 Frisbee Hill Rd., Hilton, NY (US) 14468

( * ) Notice: Subject to any disclaimer, the term of this patent is extended or adjusted under 35 U.S.C. 154(b) by 0 days.

(21) Appl. No.: 10/166,932

(22) Filed: Jun. 11, 2002

(65) Prior Publication Data

US 2003/0226778 A1 Dec. 11, 2003

(51) Int. Cl.7 ............................................. B65D 81/22
(52) U.S. Cl. ................. 206/362.2; 206/15.2; 206/209.1
(58) Field of Search ................. 206/806, 361, 206/210, 362, 362.1, 362.2, 362.3, 209, 15.2, 15.3, 209.1; 312/206, 207

(56) References Cited

U.S. PATENT DOCUMENTS

| 1,448,231 | A | | 3/1923 | Morrison |
| 1,486,957 | A | | 3/1924 | England |
| 1,696,706 | A | | 12/1928 | Athon |
| 1,708,423 | A | | 4/1929 | MacShane |
| 2,904,808 | A | * | 9/1959 | Massman ..................... 401/4 |
| 3,574,879 | A | * | 4/1971 | Werding ..................... 15/184 |
| 3,904,362 | A | | 9/1975 | DiPaolo |
| 4,527,574 | A | * | 7/1985 | Manfredi ................... 132/308 |
| 4,585,119 | A | | 4/1986 | Boyington |
| 4,884,688 | A | * | 12/1989 | Hurst ..................... 206/362.2 |
| 4,915,219 | A | | 4/1990 | Ottimo |
| 5,044,386 | A | * | 9/1991 | Nelson ..................... 132/309 |
| 5,301,799 | A | * | 4/1994 | Gurba, Jr. ..................... 206/1.7 |
| 5,566,823 | A | | 10/1996 | Summers |
| 5,984,100 | A | * | 11/1999 | Ramsey et al. ............. 206/581 |
| 5,992,617 | A | * | 11/1999 | Couch et al. ............. 206/15.3 |
| 6,050,408 | A | * | 4/2000 | Testa ......................... 206/361 |
| D424,306 | S | * | 5/2000 | Strum et al. ................. D4/121 |
| 6,360,884 | B1 | | 3/2002 | Smith et al. |
| D463,698 | S | * | 10/2002 | Phillips et al. .............. D6/524 |
| D465,957 | S | * | 11/2002 | Driscoll et al. .............. D6/551 |
| 6,516,947 | B1 | * | 2/2003 | Van Dyke et al. .......... 206/361 |

* cited by examiner

Primary Examiner—Shian Luong
(74) Attorney, Agent, or Firm—Fred L. Denson

(57) ABSTRACT

A toothbrush sanitizing assembly having a detachable toothbrush and receptacle. The receptacle is preferably cylindrically shaped with a closed base, an open top and a sidewall that extends from the base to the top. A receptacle cover is an integral part of the toothbrush and is attached to the neck of the toothbrush. Mateable threads, a snap fit mechanism or other type of detachable fastening means are positioned near the top of the receptacle sidewall and on the receptacle cover. A hook is positioned at the distal end of the toothbrush handle and/or on the receptacle sidewall for hanging the assembly in a vertical position. A flat receptacle base also allows the assembly to be free standing on a flat surface. In use, the brush head is immersed in a liquid antiseptic contained in the receptacle by fastening the cover to the receptacle with the detachable fastening means.

8 Claims, 6 Drawing Sheets

TOOTHBRUSH SANITIZING ASSEMBLY

BACKGROUND OF THE INVENTION

1. Field of the Invention

The present invention relates to a toothbrush sanitizing assembly for storing one or more toothbrushes in a receptacle containing a liquid antiseptic.

2. Description of the Prior Art

Contamination of toothbrush bristles by bacteria and other types of germs has been a long standing concern in the dental hygiene field. Toothbrush bristles are most vulnerable to contamination during between-use periods at times while the bristles are wet and the toothbrush is stored, unprotected in an area that is exposed to ambient air in or near a bathroom. Such wet bristles provide an ideal environment for invasion by airborne bacteria or other germs. Even though the bristles subsequently become dry and even though they may be thoroughly rinsed with water immediately prior to the next use, some residual contamination remains. After repeated cycles of brushing, storing and rinsing, there is the potential for contamination build-up that has an adverse impact on a user's dental care and oral hygiene.

Over the years, the level of awareness of the negative effects of bristle contamination has increased and has become widely recognized as evidenced by the issuance of a number of patents that address the problem. Some patents provide specially designed storage containers that maintain a toothbrush in a controlled environment between uses while other patents provide means for keeping a toothbrush head immersed in an antiseptic liquid between uses. U.S. Pat. No. 1,448,231 by Morrison discloses a toothbrush container for storing a toothbrush in a manner such that the brush head is submerged in an antiseptic liquid. U.S. Pat. No. 6,360,884 discloses a multi-compartment storage container that has the capacity to store several toothbrushes with their brush heads immersed in an antiseptic fluid. While immersion of a brush head in an antiseptic liquid is an efficient way to protect against contamination, some patents use a gas or vapor instead of a liquid antiseptic. Even though bristle contact by an antiseptic vapor or gas may be less efficient than bristle contact by an antiseptic liquid, the use of a gas or vapor is more convenient particularly where portability, liquid seepage or handling are a concern. U.S. Pat. No. 1,486,957 by England, U.S. Pat. No. 1,696,706 by Athon and U.S. Pat. No. 1,708,423 by Mac Shane, each disclose toothbrush containers that store brush heads in a gaseous or vaporous antiseptic environment.

The prior art discloses many other types of containers for storing toothbrushes under sanitary conditions. U.S. Pat. No. 3,904,362 by DiPaulo shows a toothbrush holder having a compartmentalized body with individual holders to immerse toothbrush bristles in an antiseptic fluid. U.S. Pat. No. 5,566,823 by Summers discloses a container with a cap having a removable tray with separate compartments for insertion of bristles into an antiseptic fluid. U.S. Pat. No. 4,585,119 by Boyinton discloses containers for holding a toothbrush neck downward in an antispetic fluid. U.S. Pat. No. 4,915,219 by Ottimo discloses a container having a plurality of compartments for storing several toothbrushes in an antiseptic fluid.

While each of these patents addresses an existing problem involving some aspect of brush head germ contamination, none of the patents discloses a device which combines the advantages of using an antiseptic liquid for treating a brush head with the advantages of using an antiseptic in vaporous form for this purpose. Those patents that utilize a liquid antiseptic benefit from the effectiveness of the contact between the liquid medium and the brush head bristles but are subject to disadvantages caused by leakage, by unwanted liquid drainage when the toothbrush is used and by the inconvenience of handling a liquid. The patents that use a vaporous antiseptic medium have the advantage of handling convenience since there is no concern about leakage between uses or liquid drainage during use. However, exposure of a brush head to an antiseptic vapor is not as effective as immersing a brush head in an antiseptic liquid because of the lower concentration of the active antiseptic substance in the vapor compared to the liquid. Moreover, such devices do not have means for maintaining the gaseous phase under increased pressure, which would permit the concentration of the antiseptic substance to be increased. Also, devices that use antiseptic vapors generally require more components than liquid devices which effects the cost of the item.

It is therefore an object of this invention to provide a toothbrush sanitizing assembly that utilizes liquid antiseptic.

It is another object of the invention to provide a toothbrush sanitizing assembly that utilizes a liquid antiseptic that is not subject to leakage during storage periods.

It is a further object of the invention to provide a toothbrush sanitizing assembly that utilizes a liquid antiseptic that protects the user against unwanted liquid contact and liquid drainage during use.

It is yet another object of the invention to provide a toothbrush sanitary assembly that is readily transportable and convenient to store between uses.

SUMMARY OF THE INVENTION

In accordance with the present invention, a toothbrush sanitizing assembly is provided for storing a brush head in a liquid antiseptic to reduce bristle contamination by bacteria or other types of germs. The assembly includes a detachable toothbrush and receptacle. The receptacle preferably is cylindrically shaped with a closed base, an open top and a sidewall that extends from the base to the top. The cover for the top of the receptacle is an integral part of the toothbrush and is positioned around the neck of the toothbrush. Detachable fastening means such as a set of threads or a snap fit mechanism are positioned near the top of the receptacle sidewall and on the receptacle cover. The assembly includes a hook positioned at the outboard or distal end of the handle and/or a hook positioned on the sidewall of the receptacle. Each hook is oriented in a manner that permits the assembly to be vertically suspended when either hook is engaged with a support hanger. In an alternative embodiment, a flat receptacle base is provided which allows the assembly to be free standing on a flat surface such as a counter top, thereby eliminating the need for hooks.

The assembly is used by filling the receptacle with a liquid antiseptic, immersing the brush head into the antiseptic by attaching the cover to the receptacle and securing the cover in place with the threaded or snap fit fastening means. When the toothbrush is readied for use, it is detached from the receptacle thereby removing the brush head from the liquid antiseptic. The receptacle cover not only encloses the receptacle during storage in a leak proof manner, but also shields the hand of the user from unwanted liquid drainage during removal and brushing by deflecting any liquid over the conically shaped surface of the cover.

The invention, its objects and advantages will become apparent in the detailed description of the preferred embodiments.

DETAILED DESCRIPTION OF PREFERRED EMBODIMENTS

Figure 1:
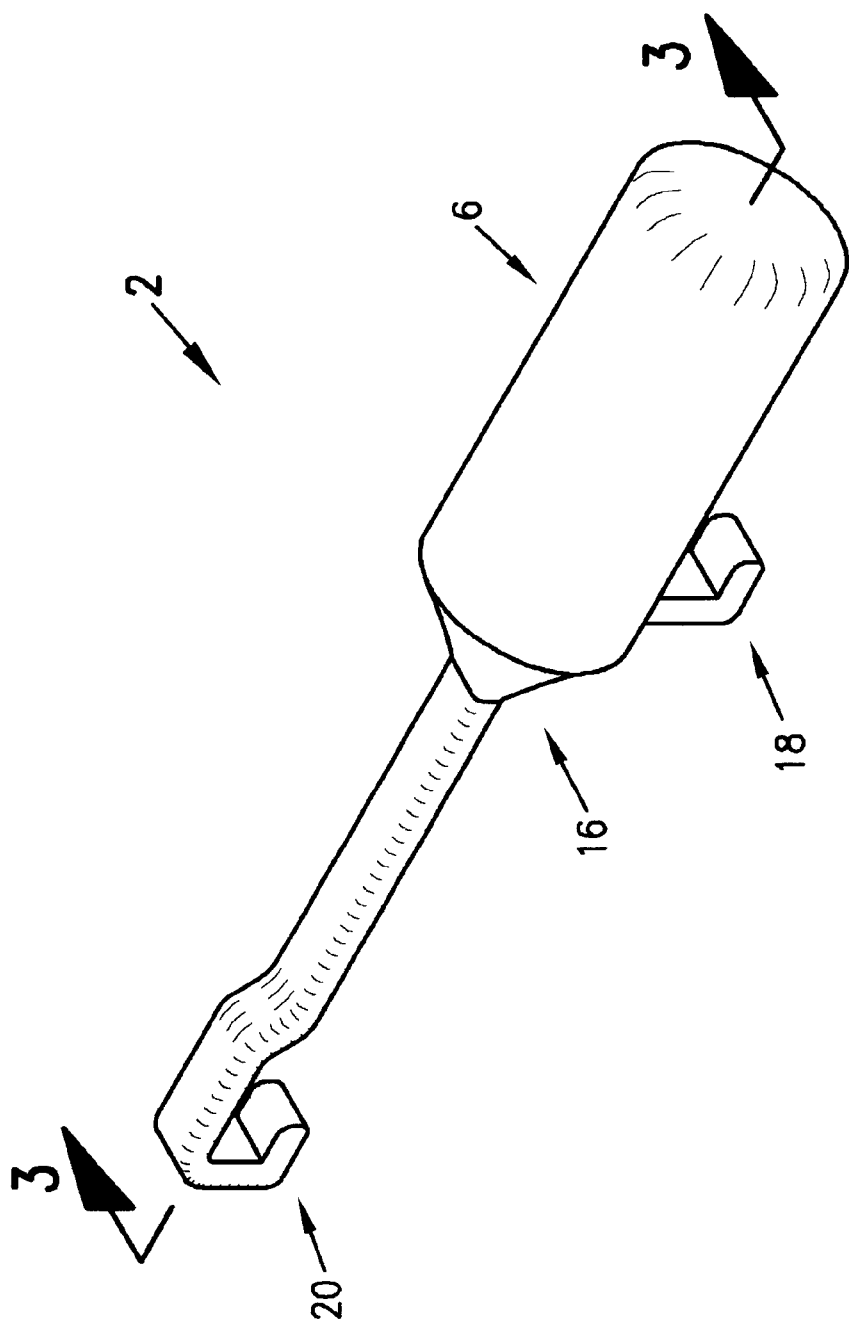
FIG. 1 is an isometric view of the toothbrush sanitizing assembly of this invention with support hooks.
Figure 2:
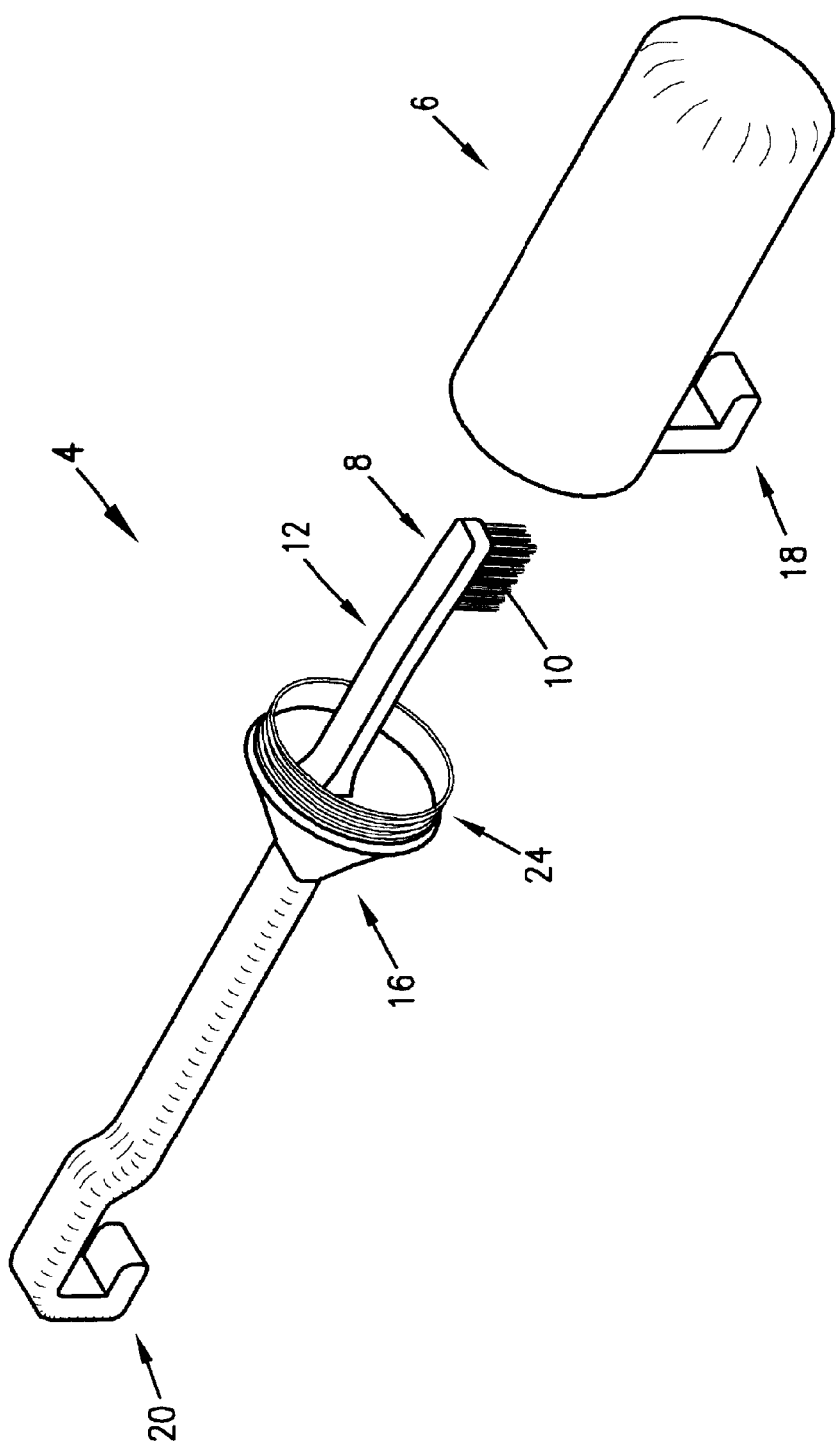
FIG. 2 is an exploded isometric view of the assembly shown in FIG. 1 with a threaded fastening means.
Figure 3:
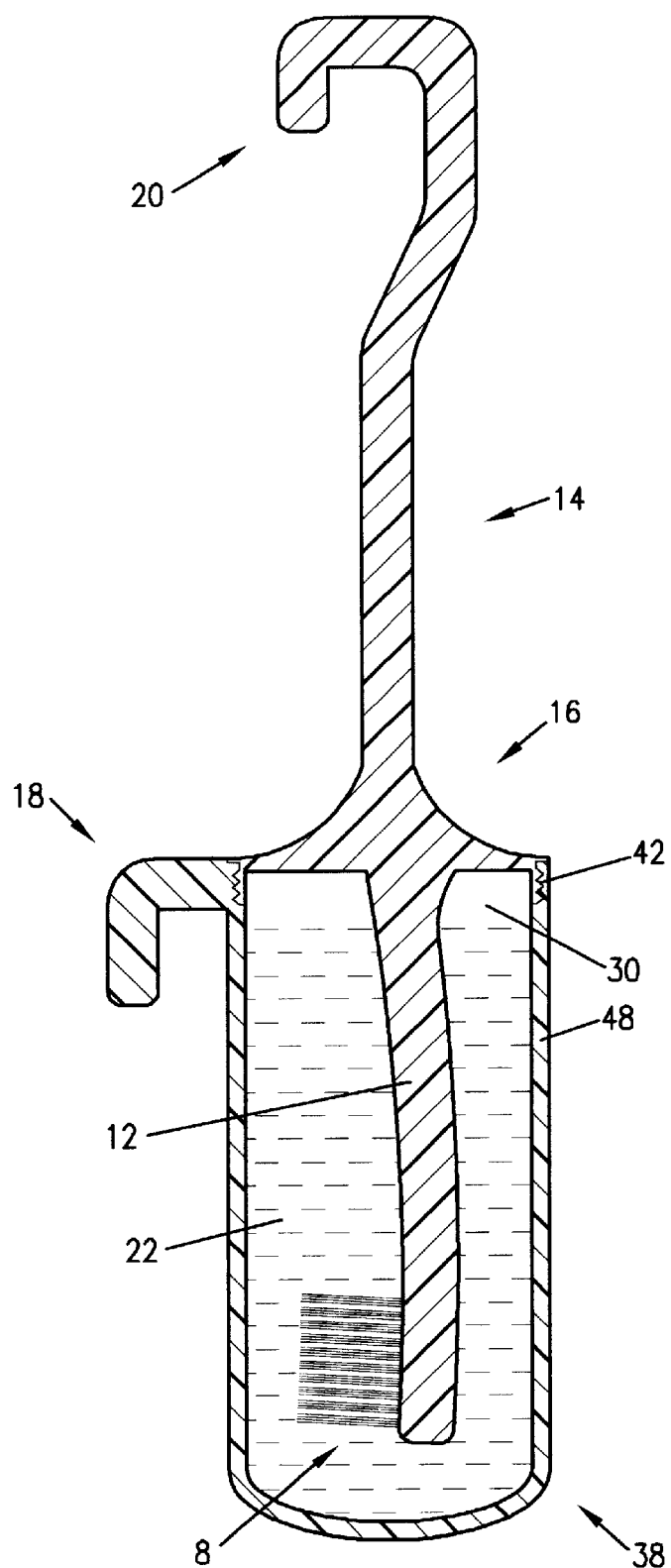
FIG. 3 is a sectional view taken along 3—3 of the assembly shown in FIG. 1 with threaded fastening means.
Figure 5:
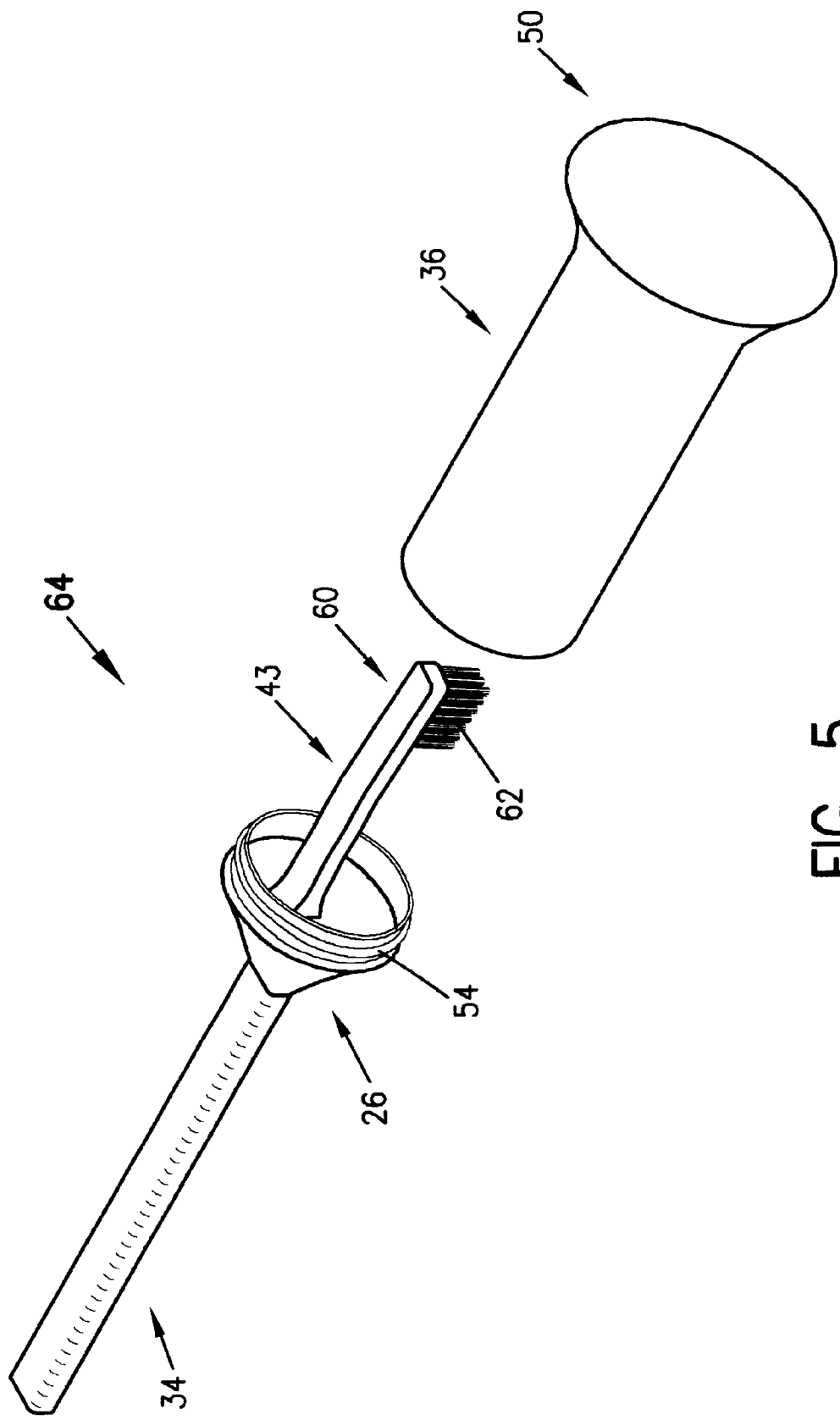
FIG. 5 is an exploded isometric view of the assembly shown in FIG. 4 with a snap fit fastening means.
Figure 6:
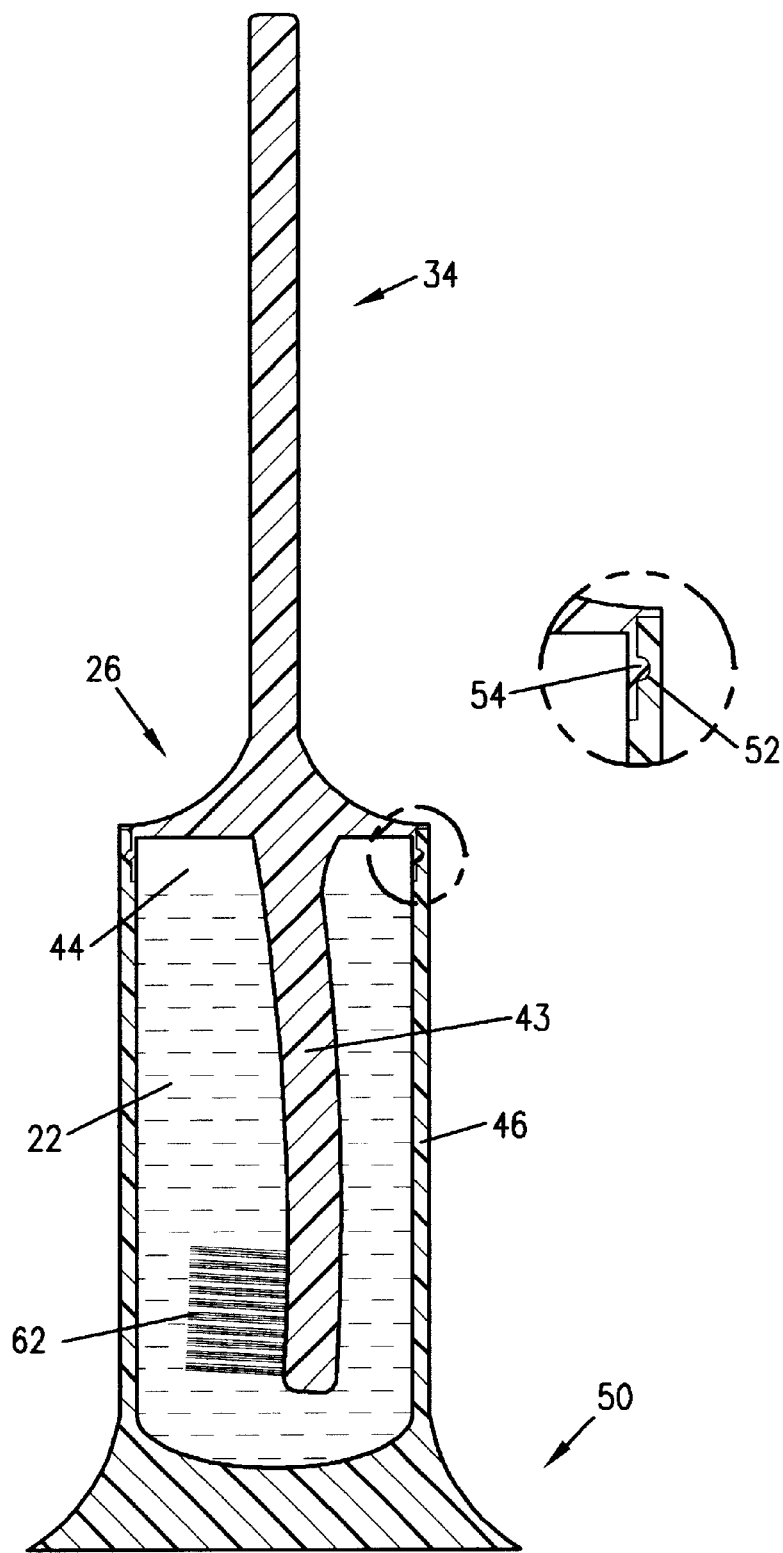
FIG. 6 is a sectional view taken along 6—6 of the assembly shown in FIG. 4 with a snap fit fastening means.

As shown in FIGS. 1, 2 and 3, toothbrush sanitizing assembly 2 of this invention includes toothbrush 4 and receptacle 6. Toothbrush 4 includes brush head 8, handle 14 and neck 12 which is connected to brush head 8 and the inboard end of handle 14. Hook 20 is integrally attached to the distal end of handle 14 while bristles 10 extend from the platform of brush head 8. Receptacle 6 includes sidewall 48 that extends from receptacle base 38 to open top 30. Outwardly projecting hook 18 is integrally attached to the upper part of receptacle side wall 48. Receptacle cover 16 is integrally attached to neck 12 in a manner such that the part of neck 12 connected to handle 14 projects from the top of cover 16 while the part of neck 12 connected to brush head 8 projects from the bottom of cover 16. The top of cover 16 is preferably cone shaped such that the inboard end of handle 14 and cover 16 are attached at the cover apex. Threads 24 positioned along the outer periphery of the bottom of cover 16 and corresponding threads 42 positioned on sidewall 48 adjacent to open top 30 of receptacle 6 provide means for attaching and detaching toothbrush 4 from receptacle 6. Brush head 8 is immersed in antiseptic liquid 22 when cover 16 is attached to receptacle 6 so that antiseptic liquid 22 is in contact with bristles 10 to remove bacteria and other types of germs from the bristles. Instead of threads 24, other types of fastening means such as the snap fit comprising mateable notch 54 and groove 52 as shown in FIGS. 5 and 6, can be used to attach toothbrush 4 and receptacle 6. When not in use, the assembly can be stored in a vertical position by using hook 20 or hook 18 to suspend it from an appropriate support. Vertical storage ensures that bristles 10 remain completely immersed in antiseptic liquid 22 during storage periods.

Figure 4:
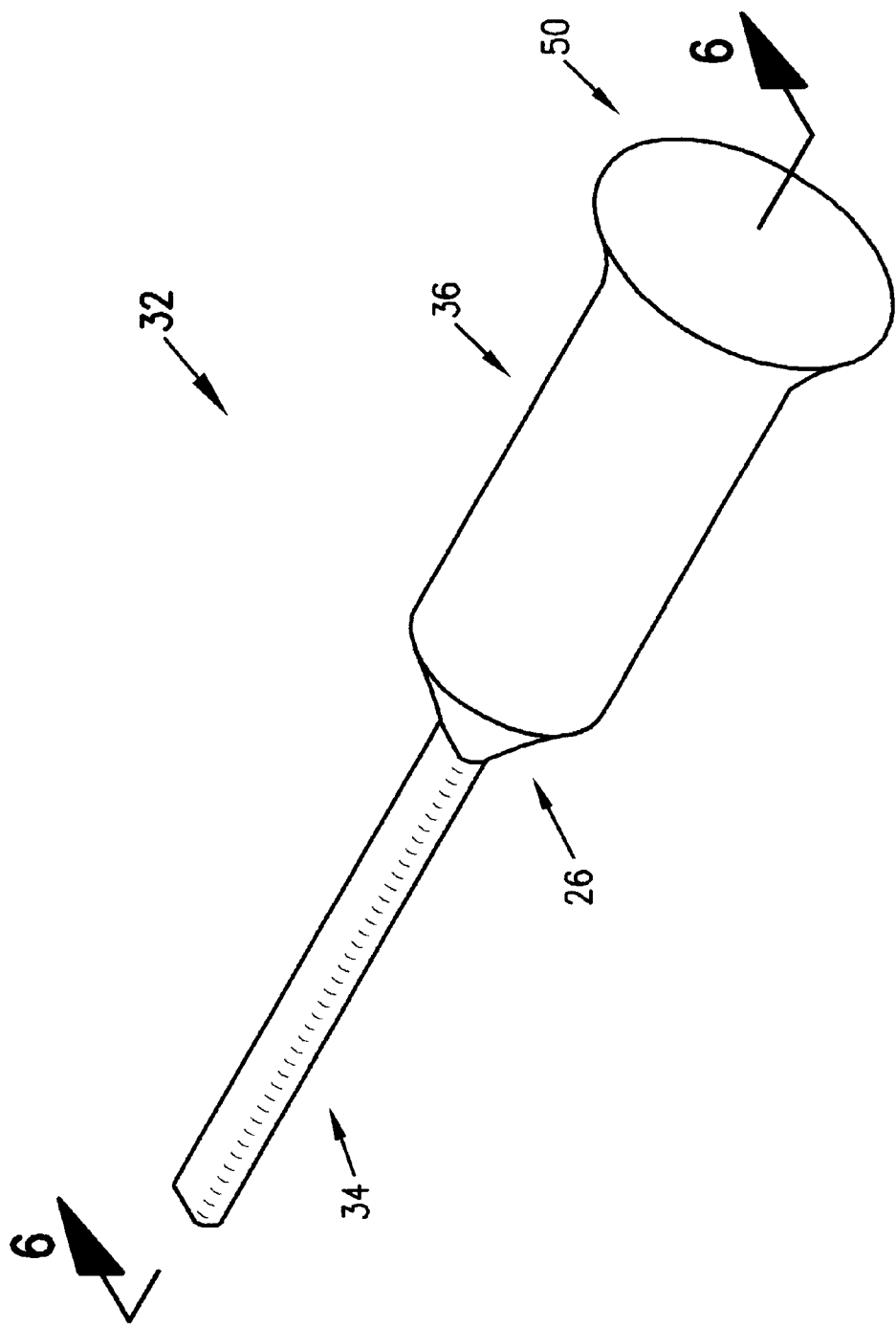
FIG. 4 is an isometric view of another embodiment of the invention showing a toothbrush sanitizing assembly having a flat base and no support hooks.

As shown in FIGS. 4, 5 and 6, toothbrush sanitizing assembly 32 is configured as a free standing structure that is designed to rest on a flat surface rather than be suspended by hooks. In this embodiment, the assembly consists of toothbrush 64 and receptacle 36. Toothbrush 64 includes brush head 60 with attached bristles 62 and handle 34 that are connected by neck 43. Receptacle cover 26 is integrally attached to neck 43 and functions in the same manner as the corresponding parts described in FIGS. 1, 2 and 3. Toothbrush 64 and receptacle 36 are detachably fastened to each other by mateable notch 54 and groove 52, which are snap or press fitted together. As previously discussed, these parts may alternatively be detachably fastened by threading or other suitable fastening means positioned along the base of receptacle cover 26 and along sidewall 46 of receptacle 36 near its open top 44. Receptacle base 50 has a flat bottom that allows the assembly to be stored as a free standing unit. Its stability in the free standing position is enhanced by the weight of disinfecting liquid 22 and the outwardly flared shape of base 50.

Receptacles 6 and 36 can be of any shape but a cylindrical shape is preferred. When receptacles 6 and 36 are attached to toothbrushes 4 and 64 respectively, the parts are efficiently sealed at their threaded or snap fit juncture to prevent leakage of any antiseptic liquid. However, a suitable gasket, washer, O-ring or other additional sealing means may be inserted at the juncture to further protect against leakage. When toothbrush 4 or 64 is removed from receptacle 6 or 36 and readied for use, the shape and positioning of cover 16 or 26 function as a shield to protect a user's hand from contact by any antiseptic liquid or dentifrice material that may drain from brush head 8 or 60 and along neck 12 or 43. The shielding function results from the receptacle cover being an integral part of the toothbrush rather than a part of the receptacle.

The receptacle and toothbrush can be fabricated from the same or different materials such as plastic, glass, metal and the like. However, a moldable thermoplastic material such as polyethylene, polypropylene, acrylic resins or other similar materials that are compatible with commercially available liquid antiseptics are preferred.

The assembly's use cycle includes storage, preparation for brushing, brushing and preparation for storage. In preparing the assembly for the storage phase of the use cycle, the receptacle is filled with a sufficient quantity of an antiseptic liquid such as Listerine® to ensure that the bristles of the brush head are completely immersed in the liquid antiseptic. Thereafter, the brush head is inserted in the receptacle, and the receptacle cover, which is a part of the brush handle, is securely attached to the receptacle by engaging the snap fit mechanism or by screwing together the threaded parts of the cover and the top of the receptacle. The receptacle is then stored in an upright, vertical position either a) by suspending the assembly by engaging one of its hooks (FIG. 1) with a suitable hanging device or b) by standing the receptacle base (FIG. 4) on a flat surface such as a counter top. Because the assembly is stored in a vertical position, the brush head remains completely immersed in the liquid antiseptic during the storage period. Even if the assembly is temporarily placed in a horizontal position for travel purposes, there is a sufficient volume of liquid in the receptacle to provide antiseptic conditions both by liquid contact with the immersed bristles and by vapor contact with any bristles or parts thereof not in direct contact with the liquid. Upon completion of the storage period, the toothbrush is readied for use by detaching the receptacle cover and removing the toothbrush. Dentifrice material is deposited on the bristles and the toothbrush is then used for brushing. Because the receptacle cover is an integral part of the toothbrush handle, the cover shields and protects the user's hand from drainage of the liquid antiseptic or brushing medium during use. The unwanted liquid flows over the outer surface of the conically shaped cover. When brushing is completed, the receptacle is refilled with liquid antiseptic, the brush head is cleaned with water and once again inserted into the receptacle where it is stored until the next use.

The toothbrush sanitizing assembly described herein is convenient to use and to store which make it user friendly. Moreover, its size and structure with only two components make it readily transportable during travel periods. It is also economical to make and safe and efficient to use.

The invention has been described in detail with reference to preferred embodiments thereof However, it is understood that variations and modifications can be effected within the spirit and scope of the invention.

I claim:

1. A toothbrush sanitizing assembly comprising:
   a. a receptacle for storing a toothbrush head in an antiseptic liquid, said receptacle consisting essentially of a sidewall, a closed base and an open top;
   b. a detachable toothbrush having
      i. a brush head,
      ii. a handle having an inboard end and a distal end,
      iii. a neck that connects the brush head to the handle,
      iv. a set of bristles that are attached to the brush head and are substantially perpendicular to the longitudinal axis of the toothbrush neck, and
      v. a cover for the open top of the receptacle that is integral to the neck, said cover having a top and a bottom, and said cover being positioned such that the part of the neck connected to the handle projects from the top of the cover and the part of the neck connected to the brush head projects from the bottom of the cover; and
   c. means for detaching the toothbrush and the receptacle.

2. The assembly of claim 1 wherein the receptacle is a cylinder having a sidewall, a closed base and an open top.

3. The assembly of claim 2 wherein the means for detaching the toothbrush and the receptacle is a set of corresponding threads positioned on the receptacle sidewall and bottom of the cover.

4. The assembly of claim 1 wherein the means for detaching the toothbrush and the receptacle is a mateable snap fit notch and groove positioned on the receptacle sidewall and bottom of the cover.

5. The assembly of claim 1 wherein a hook is integrally attached to the distal end of the handle.

6. The assembly of claim 1 wherein the top of the cover for the receptacle is cone shaped, said top being positioned such that its apex is integral with the inboard end of the handle.

7. The assembly of claim 1 wherein the receptacle base is flat.

8. The assembly of claim 1 wherein a hook is integrally attached to the receptacle side wall and projects outwardly from said receptacle side wall.

* * * * *